| United States Patent [19] | [11] | 4,101,330 |
| Burk et al. | [45] | Jul. 18, 1978 |

[54] LEUCITE-CONTAINING PORCELAINS AND METHOD OF MAKING SAME

[75] Inventors: Bruce Burk, Windsor, Conn.; Arthur P. Burnett, Milford, Del.

[73] Assignee: The J. M. Ney Company, Bloomfield, Conn.

[21] Appl. No.: 719,380

[22] Filed: Sep. 1, 1976

[51] Int. Cl.$^2$ .................... C04B 35/14; C04B 33/00; C04B 33/24

[52] U.S. Cl. .......................................... 106/45; 106/35

[58] Field of Search ............................. 106/45, 46, 35

[56] References Cited

U.S. PATENT DOCUMENTS

| 2,334,319 | 11/1943 | Erdle | 106/45 |
| 3,585,056 | 6/1971 | Bish | 106/45 |
| 3,651,184 | 3/1972 | Everhart et al. | 106/45 |

*Primary Examiner*—Winston A. Douglas
*Assistant Examiner*—Mark Bell

[57] ABSTRACT

A ceramic raw material essentially contains a preformed leucite filler which is obtained by reacting alumina, silica and potassium carbonate and/or oxide at a temperature of at least 1149° C, and nepheline syenite. A leucite-nepheline syenite ceramic raw material which is useful as a dental porcelain powder contains 14 percent by weight of sodium-, potassium-, and lithium carbonates and 86 percent by weight of a 5 percent leucite/95 percent nepheline syenite mixture.

Upon fusing of the ceramic raw material of the invention, ceramic bodies are formed which have a crystalline leucite phase dispersed in a matrix of a glassy nepheline phase and any other constituents of the ceramic. The leucite provides the ceramic bodies with desirable properties of controlled thermal expansion and high strength.

25 Claims, No Drawings

LEUCITE-CONTAINING PORCELAINS AND METHOD OF MAKING SAME

BACKGROUND OF THE INVENTION

The present invention is concerned with ceramics, and more particularly with a nepheline syenite and leucite-containing ceramic raw material and ceramic bodies made therefrom. Although not limited thereto, the invention has particular application to a ceramic raw material comprising a dental porcelain powder and to dental porcelain made therefrom, which porcelain has a nepheline syenite glassy phase matrix in which is dispersed a crystalline leucite.

The use of nepheline syenite in dental porcelains as a replacement for feldspar is known, as shown in *The Ohio State University Eng. Exp. Sta. Bulletin* 118, Mar. 19, 1944 and U.S. Pat. No. 2,334,319. The use of nepheline syenite in glass or for other ceramic purposes has also been suggested. *Am. Mineralogist* 31, 284–87 (1946).

Leucite is a naturally occurring mineral which heretofore has not been considered to be commercially important (see *Ceramic Industry Magazine*, page 76, January, 1974) and is not believed to be available in commercial quantities. Insofar as is known, leucite has not been included in ceramic compositions although it is conceivable that isolated colonies of leucite may be formed in some ceramics during fusing thereof. Laboratory preparation of leucite has been reported in the literature, *American Journal of Science*, Vol. 253, December 1955. pp. 681–746. Also see, *J. Chem Soc.* 1955, 2480-1, abstracted in *Chemical Abstracts*, Volume 49, columms 13727–13728.

In providing ceramic raw materials and the ceramic bodies made therefrom, it is generally desirable that the body have characteristics of good strength, thermal expansion and appearance. (As used herein and in the appended claims, the term "ceramic raw material" means the ingredients which are fired to form ceramic bodies, and the term "porcelain" has its usual meaning of a white, fine grade of ceramic.) Strength and thermal expansion characteristics are particularly important in ceramics used in applications such as dental porcelain. In dental porcelains, thermal expansion and other characteristics of the porcelain must be rigidly controlled to insure good bonding of the porcelain to the metal components of the dental prosthesis and control of the exacting dimension and configuration requirements. Obviously, high strength and controllable thermal expansion characteristics are generally desirable characteristics in any use to which the ceramic is put.

It is accordingly an object of the present invention to provide a novel ceramic raw material composition which, when fused, provides a ceramic body of high strength and rigidly controllable thermal expansion characteristics.

It is another object of the present invention to provide a novel ceramic raw material composition essentially containing leucite and nepheline syenite and a novel method of making ceramic bodies using the composition.

It is yet another object of the present invention to provide a novel ceramic body which includes a leucite crystalline phase dispersed in a matrix of a glassy nepheline syenite phase and possibly other ingredients, which provides the ceramic body with high strength and controllable thermal expansion characteristics.

It is yet another object of the present invention to provide a ceramic raw material containing a pre-formed synthetic, i.e., manufactured, leucite and ceramic bodies made therefrom in which the leucite in combination with the other ingredients provides the ceramic bodies with high strength, good appearance, and good controllable thermal expansion characteristics which are well suited for use as dental porcelains.

Another object of the invention is to provide a novel method for making ceramic bodies which are suited for use as the porcelain component of dental prostheses.

Other objects and advantages of the present invention will become apparent from the following description.

SUMMARY OF THE INVENTION

A ceramic raw material is essentially an admixture of nepheline syenite and about 3 to 7 percent by weight of fine particles of pre-formed leucite dispersed as a filler in the material. The material may further include one or more modifiers consisting of oxides and oxide precursors of potassium, sodium and lithium. At least one each of such potassium, sodium and lithium modifier compounds are included in the material to attain certain objects of the invention. The modifier compounds are preferably oxides and/or carbonates of potassium, sodium and lithium.

Other objects of the invention are obtained by providing a ceramic body which comprises about 3 to 7 percent by weight of leucite dispersed as fine particles in a glassy nepheline syenite matrix, the ceramic body being characterized by being substantially free of quartz particles. The leucite particles preferably have a diameter of not more than about 37 microns and are dispersed substantially uniformly throughout the nepheline syenite glassy phase.

Other objects of the invention are attained by providing a ceramic body comprising about 93 to 97 percent by weight of a modified nepheline syenite glassy phase and about 3 to 7 percent by weight of leucite particles.

The invention also provides a dental prosthesis which includes as the porcelain component thereof the ceramic body of the invention.

Other objects of the invention are attained by a method for the production of the ceramic raw material which method includes the steps of preparing leucite particles by heating an admixture of alumina, silica and a potassium compound. The potassium compound may be potassium oxide, potassium carbonate or mixtures thereof. The admixture is heated to a temperature of at least about 1149° C for a time sufficient to form leucite. The leucite particles so obtained are admixed with nepheline syenite with or without modifiers to form a ceramic raw material containing about 3 to 7 percent by weight of leucite.

A method for the production of a ceramic body is also provided wherein the ceramic raw material of the invention is heated at a temperature high enough to fuse the nepheline syenite but below the fusing temperature of leucite. The heating material is cooled to form a ceramic body having a crystalline leucite phase dispersed in a nepheline syenite glassy phase.

DESCRIPTION OF THE PREFERRED EMBODIMENTS

Generally, ceramic raw materials, by which term is meant the materials which are heated and fused to form a ceramic body, include one or more plastic clays and/or nonplastic minerals, which together usually comprise the bulk of the finished ceramic body, and one or more refractory fillers such as alumina which add bulk to and strengthen the finished ceramic body. In addition, other ingredients, which will be referred to herein as "modifiers," may be added to impart specific characteristics to the finished ceramic body.

The ceramic raw material of the present invention may include one or more of the foregoing ingredients, but it essentially contains, in addition to nepheline syenite, leucite which is prepared in advance and added to the raw material as a component thereof so that ceramic bodies of the invention essentially comprise a glassy matrix phase (formed by the other ingredients) in which is dispersed a crystalline leucite. The other ingredients include nepheline syenite as a major constituent to form a glassy nepheline phase.

Nepheline syenite is a naturally occurring granular mineral composed largely of alkali feldspar, nepheline and a dark colored material which is mostly iron. Nepheline is a mineral of the feldspathoid group and is essentially a sodium/potassium aluminosilicate. Commercially available nepheline syenite used for the preparation of ceramic raw materials is in powder or granular form and has been refined to the extent of having the dark colored materials removed. The dark colored materials are mostly magnetic forms of iron and the usual mode of refining the nepheline syenite includes removal of the iron components by magnetic treatment. The refined nepheline syenite thus largely comprises an aluminosilicate which is rich in alkali metal, primarily sodium and potassium.

When melted, i.e., fused, by heating at a suitable temperature, the nepheline syenite forms a glassy substance hereinafter sometimes referred to as nepheline glass. The composition of the nepheline glass may be altered by the addition to the ceramic raw material of suitable modifiers which react with the nepheline syenite. For example, the sodium, potassium and lithium content of the nepheline glass may be adjusted by the addition of suitable amounts of oxides or carbonates of sodium, potassium and lithium to the nepheline syenite. Upon fusing of the mixture, these react with the nepheline syenite. Other oxygen-containing compounds of sodium, potassium and lithium such as borates, oxalates, etc., may also be employed.

Depending on the end use and the properties desired in the ceramic body, the ceramic raw material of the invention may contain up to about 97 percent by weight nepheline glass. For example, in one embodiment of the ceramic raw material of the invention, nepheline glass comprises between about 93 percent to 97 percent by weight of the composition with leucite comprising the balance. The ceramic body produced therefrom is well suited for use as a dental porcelain.

Leucite is a naturally occurring feldspathoid having the nominal chemical formula $K_2O.Al_2O_3.4SiO_2$. Aside from commercial unavailability of natural leucite, it is anticipated that impurites and variations in compositions would render the natural leucite inferior to that made in accordance with the invention for the purposes of the invention. The leucite synthesized in the manner described herein has a controllable composition. By comminuting the mass obtained by heating the leucite-forming indredients, a granulated or powdered synthetic leucite of regular particle size and controlled composition is obtained. The leucite so prepared provides distinct advantages when employed as a filler for ceramic bodies. The leucite is refractory and retains its crystalline structure at the fusing temperatures of nepheline syenite and other fusible minerals employed in the new ceramic raw material. The leucite thus provides a crystalline filler for the nepheline glass matrix and results in a high strength ceramic material with good, controllable thermal expansion characteristics.

The leucite is prepared by heating an admixture of alumina, silica and potassium oxide and/or potassium carbonate (or other materials containing the foregoing) to a temperature of at least about 1149° C, and maintaining the admixture at that temperature for a period of time sufficient to react the ingredients to form leucite. Generally, increasing the reaction temperature will increase the percentage conversion of the ingredients to leucite. Accordingly, heating the admixture to a temperature of above 1149° C, preferably to about 1538° C or even higher, is preferred. The higher temperatures may be up to temperatures below about 1871° C, the low end of the fusing temperature range of leucite, which is about 1871° to 1982° C. A portion at least of the ingredients will react at the elevated temperature to form crystalline leucite having the formula $K_2O.Al_2O_3.4SiO_2$. The leucite crystal is generally tetragonal.

The material must be held at the reaction temperature for a period of time to allow the reaction to take place. Generally, it has been found that holding the material at the reaction temperature for at least about two hours will provide approximately the maximum percentage conversion of the ingredients to leucite which is attainable for those particular ingredients at that temperature.

While the starting materials may be alumina, silica and potassium oxide or carbonate, other ingredients which contain or comprise these compounds may also be employed. For example, any of the various types of kaolin may be employed. Kaolin is a term applied to any of a group of clay minerals such as kaolinite, nacrite, pickite and anauxite which are characterized by having a two-layer crystal of the approximate composition $Al_2O_3.2SiO_2.2H_2O$. An admixture for the preparation of leucite in accordance with the invention may comprise a mixture of kaolin and potassium carbonate. Other admixtures may also be used. The potassium carbonate (and other alkali metal carbonates) will decompose to the corresponding oxide upon being heated to the temperatures employed. So long as the admixture includes the leucite forming ingredients, some extraneous minerals may also be present.

The formation of leucite is favored not only by increased reaction temperature but by providing the admixed ingredients in extremely fine particle sizes and thoroughly mixed. The small particle size and thorough mixing of the ingredients provide an extremely large surface area of ingredients in intimate contact which promotes the reaction. It has been found that providing the ingredients, or at least a substantial portion of them, in the form of particles having a diameter of about five microns or less substantially enhances the percentage of conversion of the ingredients to leucite.

Some ingredients such as certain clays have been found to be less reactive than others in terms of forming leucite and required higher temperature levels than other ingredients to provide satisfactory yields of leucite. Further, it has been found that some clay materials, particularly when fused at relatively low temperatures, react to form kaliophylite which has the nominal formula $K_2O.Al_2O_3.2SiO_2$. For example, an admixture of china clay with potassium carbonate will react at temperatures as low as about 952° C but at that temperature will form kaliophylite. This admixture must be reacted at temperatures of at least about 1260° C to yield leucite. Thus, depending on the materials employed, a certain minimum temperature level for leucite formations is required.

The leucite-forming ingredients may be mixed in the molar ratios required to yield leucite, i.e., 1:1:4 of alumina; potassium compound: silica. This is not essential however, and is not always feasible when mixtures containing naturally occuring ingredients such as kaolin are employed. While excess amounts of potassium compound and silica could be leached from the final leucite product, this added step is expensive and normally not necessary. The reason is that unreacted components of the leucite forming admixture, whether present because of an unbalanced molar ratio (in terms of forming leucite) or because of incomplete reaction, can usually usefully serve as another filler in the ceramic raw material. However, for use as dental porcelains, preparation of leucite from alumina, the potassium compound and silica is preferred since it is easier thereby to control the color and luster of the finished product which is of prime importance in dental porcelains. For the same reason, most preferably the alumina potassium compound and silica are prepared in the required molar ratios.

Among the specific embodiments of the invention are a dental porcelain powder advantageously comprising 3 to 7 percent by weight leucite, preferably 5 percent, the balance being a modified nepheline glass. The modified nepheline glass is made from a mixture of between about 12 to 16 percent by weight, most preferably 14 percent, of sodium carbonate, potassium carbonate and lithium carbonate, with the balance comprising nepheline syenite. The sodium, potassium and lithium may be added in the form of oxides, or as other oxygen-containing compounds. This provides an admixture of at least about 78.1 percent by weight nepheline syenite, 3 to 7 percent by weight leucite particles and up to 15.5 percent by weight of the modifiers selected from the group consisting of oxides and oxide precursors of potassium, sodium and lithium. The sodium-potassium-and lithium compounds are added in porportion such that when calculated as the respective carbonates:

(1) the ratio of sodium carbonate to potassium carbonate is not greater than 0.54;

(2) lithium carbonate is not more than 25 percent by weight of the mixture of sodium-, potassium-, and lithium carbonate;

(3) lithium carbonate is not less than 20 percent by weight of the sodium-, potassium-, and lithium carbonate; and (4) potassium carbonate is not more than 55 percent by weight of the sodium-, potassium-, and lithium carbonate.

If either condition (1) or (2) is not satisfied, the leucite will tend to dissolve in the modified nepheline glass.

If condition (3) is not satisfied, the fusing temperature will be too high for satisfactory use as a dental porcelain.

If condition (4) is not satisfied, the thermal expansion and/or the fusing temperature of the composition will be too high for satisfactory use as a dental porcelain.

The following examples are exemplary of the efficacy of the invention

EXAMPLE 1

The kaolin mixes shown below were prepared by adding saturated (except for mix no. 11) aqueous potassium carbonate solution to kaolin powder and mixing the ingredients in a muller-type mixer for 20 to 30 minutes until a highly uniform mixture was obtained. Hot air was applied during mixing to drive off excess moisture. The amount of solution added had to be limited in some cases to keep the mixtures from becoming too wet. The pellets are heated in an electric furnace to 1227° C in about 10 hours and soaked at that temperature for an additional two hours. The fired pellets are ground and analyzed by X-ray diffraction by comparing the major leucite peaks in the sample to the same peaks of a standard leucite sample. No standard kaliophilite sample was available so only the relative intensity of the kaliophilite peak is shown. This is proportional to the amount of kaliophilite present.

| Mix No. | Kaolin Type | Parts By Weight Kaolin | Parts By Weight $K_2CO_3$ | Parts By Weight of water per 100 parts Kaolin + $K_2CO_3$ | % By Weight Leucite | Relative Intensity of Peak |
|---|---|---|---|---|---|---|
| 1 | Kingsley | 80 | 20 | 20 | 30 | 20 |
| 2 | Monarch | 81.9 | 18.1 | 18.1 | 56 | 10 |
| 3 | Ajax P | 80 | 20 | 20 | 56 | 7 |
| 4 | No. 6 Tile | 81.5 | 18.5 | 18.5 | 55 | — |
| 5 | NLB Eng. China | 80 | 20 | 20 | 56 | 10 |
| 6 | Hydrite UF | 80 | 20 | 20 | 59 | 8 |
| 7 | Kaolex SH | 80 | 20 | 20 | 58 | 12 |
| 8 | Kaolex SC | 83.8 | 16.2 | 16.2 | 48 | 7 |
| 9 | Ajax SC | 80 | 20 | 20 | 72 | — |
| 10 | Kingsley | 90 | 10 | 10 | 43 | — |
| 11 | Kingsley | 90 | 10 | 17.2 | 50 | — |
| 12 | Kingsley | 80 | 20 | 20* | 55 | 10 |

*The water contains 1% by weight of methyl cellulose (Methocel).

Example 1 shows that mix no. 9 is the most successful in terms of leucite production. Local concentrations of potassium carbonate seem to favor kaliophilite production; the Methocel in mix no. 12 was added to attempt to limit migration of the potassium carbonate, and the leucite yield was improved (compare mix no. 12 to mix. no. 1). Mix no. 11 used only half as much potassium carbonate in an unsaturated solution to avoid problems of crystallization of potassium carbonate. A satisfactory leucite yield and no detected kaliophilite resulted. (Compare mix no. 11 to mix no. 1).

Preparing the leucite by wet methods, e.g., using a water solution of potassium carbonate, gives stronger finished products than does preparing the leucite by firing dry mixtures of leucite ingredients. This may be due to improved dispersal of the ingredients.

EXAMPLE 2

The following admixture is prepared by the method employed in Example 1, the quanitities being shown in parts by weight:

| | |
|---|---|
| Kingsley kaolin | 90 |
| Potassium carbonate | 10 |
| Water | 15 |

The admixture is heated to 1538° C and maintained at that temperature for over 2 hours to form leucite.

EXAMPLE 3

A leucite-forming admixture comprises the following ingredients in the form of a fine powder:

| | Parts By Weight |
|---|---|
| $K_2O$ | 25.8 |
| $Al_2O_3$ | 29.2 |
| $SiO_2$ | 45.0 |

The admixture is heated to a temperature of 1538° C and is maintained at that temperature for about 2 hours to form leucite. The cooled leucite is ground to a particle size of 37 microns or less.

EXAMPLE 4

A nepheline syenite glass has the following composition:

| | Parts By Weight |
|---|---|
| (A) Nepheline syenite | 86.0 |
| (B) Alkali metal carbonate mixture | 14.0 |

The nepheline syenite (A) is Lakefield A-400 nepheline syenite having the following composition:

| | Weight Percent |
|---|---|
| $SiO_2$ | 60.7 |
| $Al_2O_3$ | 23.3 |
| CaO | 0.7 |
| MgO | 0.1 |
| $Na_2O$ | 9.2 |
| $K_2O$ | 4.6 |
| $Fe_2O_3$ | 0.08 max. |

The Lakefield A-400 has a fusing point of 1204° C and exhibits a weight loss on ignition of about 0.7%.

The mixture of alkali metal carbonates (B) has the following composition:

| | Weight Percent |
|---|---|
| potassium carbonate | 50.3 |
| sodium carbonate | 26.7 |
| lithium carbonate | 22.9 |

The above mixture of (A) and (B) heated at about 1260° C to fuse the mixture. The fused mixture is cooled and ground in a ball mill to a powder of nepheline glass.

EXAMPLE 5

The following ingredients are provided in the form of powders:

| | Parts By Weight |
|---|---|
| The leucite of Example 3 | 5 |
| The nepheline glass of Example 4 | 95 |

The ingredients are thoroughly mixed to provide a dental porcelain powder.

EXAMPLE 6

The dental porcelain powder of Example 5 is fired at a temperature of about 1250° C to fuse the nepheline glass. Upon cooling, a dental porcelain body of the following characteristics is obtained:

Modulus of rupture is greater than 10,000 psi

| | |
|---|---|
| Thermal expansion: | 0.810 at 600° C |
| | 0.670 at 500° C |
| Fusing temperature: | 982° C |

Shrinkage between unfired (green) and fired porcelain is less than 15 percent. (Shrinkage was determined by measuring, before and after fusing, 1½ inch diameter discs made of the porcelain powder).

The inclusion of pre-formed synthetic leucite in the form of fine particles dispersed through the ceramic raw material has been found to provide certain advantageous results. The leucite so included does not react with nepheline syenite at the firing temperatures (usually 1200° to 1300° C) which are employed to fuse the nepheline syenite to form the ceramic body. This is to be contrasted with the situation obtained in prior art techniques in which leucite may be formed in situ by reaction during firing of the raw material of some of the components thereof. Such leucite forming reaction uses components of the raw materials resulting in a loss of control of the final composition, often with disadvantageous results. Further, the leucite colonies so formed are of irregular and sometimes quite large size. The ceramic structures resulting show numerous microcracks as well as quartz crystals therein. The microcracks tend to weaken the resultant ceramic body.

The dispersal of pre-formed leucite particles of controlled particle size in matrix phase-forming material avoids the foregoing difficulties. It is believed that upon firing the ceramic raw material of the invention to form the ceramic bodies therefrom, the leucite expands as the nepheline syenite material melts and, upon cooling, the leucite contracts as the nepheline syenite solidifies resulting in a pre-stressed structure of enhanced strength.

Having thus described the invention, we claim:

1. A ceramic raw material consisting essentially of at least about 78.1 percent by weight nepheline syenite, about 3 to 7 percent by weight of pre-formed leucite particles and about 0 to 15.5 percent by weight of at least one modifier selected from the class consisting of oxides and oxide precursors of potassium, sodium and lithium.

2. The ceramic material of claim 1 wherein said modifiers are present in the amount of about 11.2 to 15.5 percent by weight thereof.

3. The ceramic material of claim 2, wherein at least one each of potassium, sodium and lithium modifier compounds of the defined class are included in said material.

4. The ceramic material of claim 3, wherein said potassium, sodium and lithium compounds are selected from the class consisting of oxides and carbonates.

5. The ceramic material of claim 4 wherein, exclusive of said leucite and with sodium, potassium and lithium calculated as their respective carbonates:
   (a) the total of sodium, potassium and lithium comprises about 12 to 16 percent by weight of the total weight of said nepheline syenite plus said modifiers;
   (b) the weight ratio of sodium to potassium is greater than about 0.54;
   (c) lithium comprises about 20 to 25 percent by weight of the total of sodium, potassium and lithium; and
   (d) potassium comprises not more than about 55 percent by weight of the total of sodium, potassium and lithium.

6. The ceramic material of claim 5 wherein said leucite comprises about 5 percent by weight of said ceramic material, said mixture of nepheline syenite and modifiers comprises about 95 percent by weight of said ceramic material and the total of said modifiers comprises about 14 percent by weight of said mixture of nepheline syenite and modifiers.

7. The ceramic material of claim 5 wherein said modifiers are carbonates.

8. The ceramic material of claim 6 wherein said modifiers are carbonates.

9. A ceramic body comprising leucite dispersed as particles in a glassy nepheline syenite matrix and characterized by being substantially free of quartz particles, said ceramic body consisting essentially of at least about 78.1 percent by weight nepheline syenite, about 3 to 7 percent by weight leucite particles and about 0 to 15.5 percent by weight of at least one modifier selected from the class consisting of oxides and oxide precursors of potassium, sodium and lithium.

10. The ceramic body of claim 9 wherein said leucite particles have a diameter of not more than about 37 microns.

11. The ceramic body of claim 9 wherein said leucite particles are dispersed substantially uniformly throughout said nepheline syenite glassy phase.

12. A ceramic body consisting essentially of
   (a) about 93 to 97 percent by weight of a modified nepheline syenite glassy phase;
   (b) about 3 to 7 percent by weight of leucite particles dispersed in said nepheline syenite phase; and wherein said nepheline syenite phase includes sodium, potassium and lithium in the following amounts, all calculated as the respective carbonates:
      (1) the total of sodium, potassium and lithium comprises about 12 to 16 percent by weight of the total weight of said nepheline syenite phase;
      (2) the weight ratio of sodium to potassium in said nepheline syenite phase is greater than about 0.54;
      (3) lithium comprises about 20 to 25 percent by weight of the total of sodium, potassium and lithium in said nepheline syenite phase; and
      (4) potassium comprises not more than about 55 percent by weight of the total of sodium, potassium and lithium in said nepheline syenite phase.

13. The ceramic body of claim 12 wherein said leucite comprises about 5 percent by weight of said ceramic material and said nepheline syenite phase comprises the balance.

14. The ceramic body of claim 12 wherein said leucite particles have a diameter not greater than about 37 microns and are substantially uniformly dispersed in said nepheline syenite phase.

15. The ceramic body of claim 14 wherein said ceramic body is substantially free of quartz particles.

16. In a method for the production of a ceramic material, the steps of:
   (a) preparing leucite particles by heating an admixture comprising alumina, silica and a potassium compound selected from the class consisting of potassium oxide, potassium carbonate and mixtures thereof to a temperature of at least about 1149° C for a time sufficient to form leucite, said alumina, silica and potassium compound being present in a molar ratio of about 1:4:1; and
   (b) admixing the leucite particles obtained in step (a) with a nepheline syenite composition to form a ceramic raw material containing about 3 to 7 percent by weight leucite.

17. The method of claim 16 wherein said admixture is maintained at said temperature of at least 1149° C for at least about 2 hours.

18. The method of claim 17 wherein said admixture is maintained at a temperature of about 1149° C to less than 1871° C for said at least about 2 hours.

19. The method of claim 18 wherein said admixture is maintained at a temperature of about 1149° to 1538° C for said at least about 2 hours.

20. The method of claim 18 wherein said admixture comprises a kaolin and potassium carbonate.

21. The method of claim 20 including the preliminary steps of preparing an aqueous solution of potassium carbonate and admixing said solution with kaolin to form a wet mixture comprising said admixture.

22. The method of claim 16 wherein said nepheline syenite composition includes modifiers selected from the class consisting of oxides and oxide precursors of potassium, sodium and lithium and at least one each of potassium, sodium and lithium compounds are added as said modifiers.

23. The method of claim 17 including the steps of heating the ceramic raw material at a temperature high enough to fuse said nepheline syenite composition but below the fusing temperature of said leucite, and cooling the fired material to form a ceramic body having a crystalline leucite phase dispersed in a nepheline syenite glassy phase.

24. The method of claim 23 in which said heating is carried out at a temperature of at least 1204° C but below 1871° C.

25. In a method for the production of a ceramic material, the steps of:
   (a) preparing leucite particles by heating an admixture comprising alumina, silica and a potassium compound selected from the class consisting of potassium oxide, potassium carbonate and mixtures thereof to a temperature of at least about 1149° C for a time sufficient to form leucite;
   (b) separating from the leucite particles any unreacted components of the admixture; and
   (c) admixing the leucite particles obtained in step (a) with a nepheline syenite composition to form a ceramic raw material containing about 3 to 7 percent by weight leucite.

* * * * *